United States Patent
Dunham

(10) Patent No.: US 9,751,438 B2
(45) Date of Patent: Sep. 5, 2017

(54) SEAT RESTING APPARATUS

(71) Applicant: Marlow Gene Dunham, Poughkeepsie, NY (US)

(72) Inventor: Marlow Gene Dunham, Poughkeepsie, NY (US)

(*) Notice: Subject to any disclaimer, the term of this patent is extended or adjusted under 35 U.S.C. 154(b) by 0 days.

(21) Appl. No.: 15/155,506

(22) Filed: May 16, 2016

(65) Prior Publication Data
US 2017/0050547 A1 Feb. 23, 2017

Related U.S. Application Data

(60) Provisional application No. 62/207,095, filed on Aug. 19, 2015.

(51) Int. Cl.
| A47C 7/38 | (2006.01) |
| B60N 2/48 | (2006.01) |
| A61F 9/04 | (2006.01) |

(52) U.S. Cl.
CPC ............ B60N 2/4879 (2013.01); A47C 7/383 (2013.01); A61F 9/04 (2013.01)

(58) Field of Classification Search
CPC .......... B60N 2/4879; A47C 7/383; A61F 9/04
USPC .......................... 297/392, 393, 397, 487, 488
See application file for complete search history.

(56) References Cited

U.S. PATENT DOCUMENTS

| 4,339,151 A * | 7/1982 | Riggs | A47C 7/383 297/393 X |
| 4,997,234 A * | 3/1991 | Royle | A47C 1/028 297/397 X |
| 5,015,036 A * | 5/1991 | Fergie | B60N 2/4879 297/397 X |
| 5,081,714 A * | 1/1992 | Liu | B60R 22/001 297/393 X |
| 5,345,633 A * | 9/1994 | Harnish | B60N 2/4879 297/397 X |
| 5,378,042 A * | 1/1995 | Daneshvar | A47C 7/383 297/393 X |
| 5,503,456 A * | 4/1996 | Rossini | A47C 7/383 297/397 X |
| 5,544,378 A * | 8/1996 | Chow | A47C 7/383 297/397 |
| 5,964,504 A * | 10/1999 | Hogan | B60N 2/4879 297/397 X |
| 6,266,825 B1 | 7/2001 | Floyd | |
| 6,435,617 B1 * | 8/2002 | McNair | A47C 7/383 297/397 |
| 6,484,335 B2 * | 11/2002 | Gilbert | A47C 7/383 297/397 |
| 6,575,533 B1 * | 6/2003 | Kicos | A47C 31/11 297/397 X |
| 6,607,245 B1 * | 8/2003 | Scher | A47C 7/383 297/393 |
| 6,748,615 B1 * | 6/2004 | Tiedemann | A47C 7/383 297/397 |

(Continued)

*Primary Examiner* — Rodney B White
(74) *Attorney, Agent, or Firm* — Dunlap Bennett & Ludwig PLLC

(57) ABSTRACT

A seat resting apparatus is provided. The seat resting apparatus includes a pillow connectable to a headrest of a seat by a connector. The present invention further includes a face strap having a first end and a second end. The face strap is sized to wrap around a user's face. The first end and the second end attach to the headrest of the seat, thereby securing the user's head against the pillow.

13 Claims, 4 Drawing Sheets

(56) References Cited

U.S. PATENT DOCUMENTS

| | | | |
|---|---|---|---|
| 6,782,572 B1 * | 8/2004 | Jones | A47C 7/383 297/397 |
| 6,957,462 B1 * | 10/2005 | Wilcox | A47C 7/383 297/393 |
| 7,628,456 B1 * | 12/2009 | Swartz | A47C 7/383 297/393 |
| 7,770,976 B2 * | 8/2010 | Lee | B60N 2/4879 297/397 |
| 7,909,406 B2 * | 3/2011 | Samuelsen | A47C 7/383 297/392 X |
| 8,287,045 B1 * | 10/2012 | Donohue | B60N 2/2812 297/393 X |
| 8,381,316 B2 * | 2/2013 | Edwards | A42B 1/006 297/393 X |
| 8,382,692 B1 * | 2/2013 | Chao | A47C 7/383 128/845 |
| 8,662,590 B2 * | 3/2014 | Bogen | A47C 7/383 297/393 |
| 2002/0163240 A1 * | 11/2002 | Cheng | A47C 7/383 297/397 |
| 2004/0124685 A1 * | 7/2004 | Buch | B60N 2/4879 297/393 |
| 2005/0268377 A1 * | 12/2005 | Massey | A42B 1/24 2/209.13 |
| 2006/0250015 A1 * | 11/2006 | Buck | B60N 2/4879 297/397 |
| 2008/0238174 A1 | 10/2008 | Cinquanta | |
| 2009/0195036 A1 * | 8/2009 | Timmis | B60N 2/2851 297/397 X |
| 2010/0308630 A1 * | 12/2010 | Davis | B60N 2/4879 297/391 X |
| 2011/0043025 A1 * | 2/2011 | Park | B60N 2/4879 297/393 |
| 2013/0020853 A1 * | 1/2013 | Gibson | A47C 7/383 297/464 |
| 2013/0088063 A1 * | 4/2013 | Montes | B60N 2/4882 297/393 |
| 2013/0119716 A1 * | 5/2013 | Stronconi | B60N 2/4805 297/220 X |
| 2014/0325741 A1 * | 11/2014 | Zaouk | B60N 2/4879 297/393 X |
| 2015/0203009 A1 * | 7/2015 | Swearingen | B60R 22/001 297/392 |
| 2015/0257538 A1 * | 9/2015 | MacDougall | A47C 7/383 297/217.1 |
| 2015/0298589 A1 * | 10/2015 | Zaouk | B60N 2/4879 297/393 |
| 2015/0352988 A1 * | 12/2015 | Knapp | A41D 1/00 297/393 |
| 2016/0068086 A1 * | 3/2016 | Gazit | B60N 2/4879 297/397 X |
| 2016/0250954 A1 * | 9/2016 | Gomez | B60N 2/4879 297/397 |
| 2017/0050546 A1 * | 2/2017 | Estimable | B60N 2/4879 |

* cited by examiner

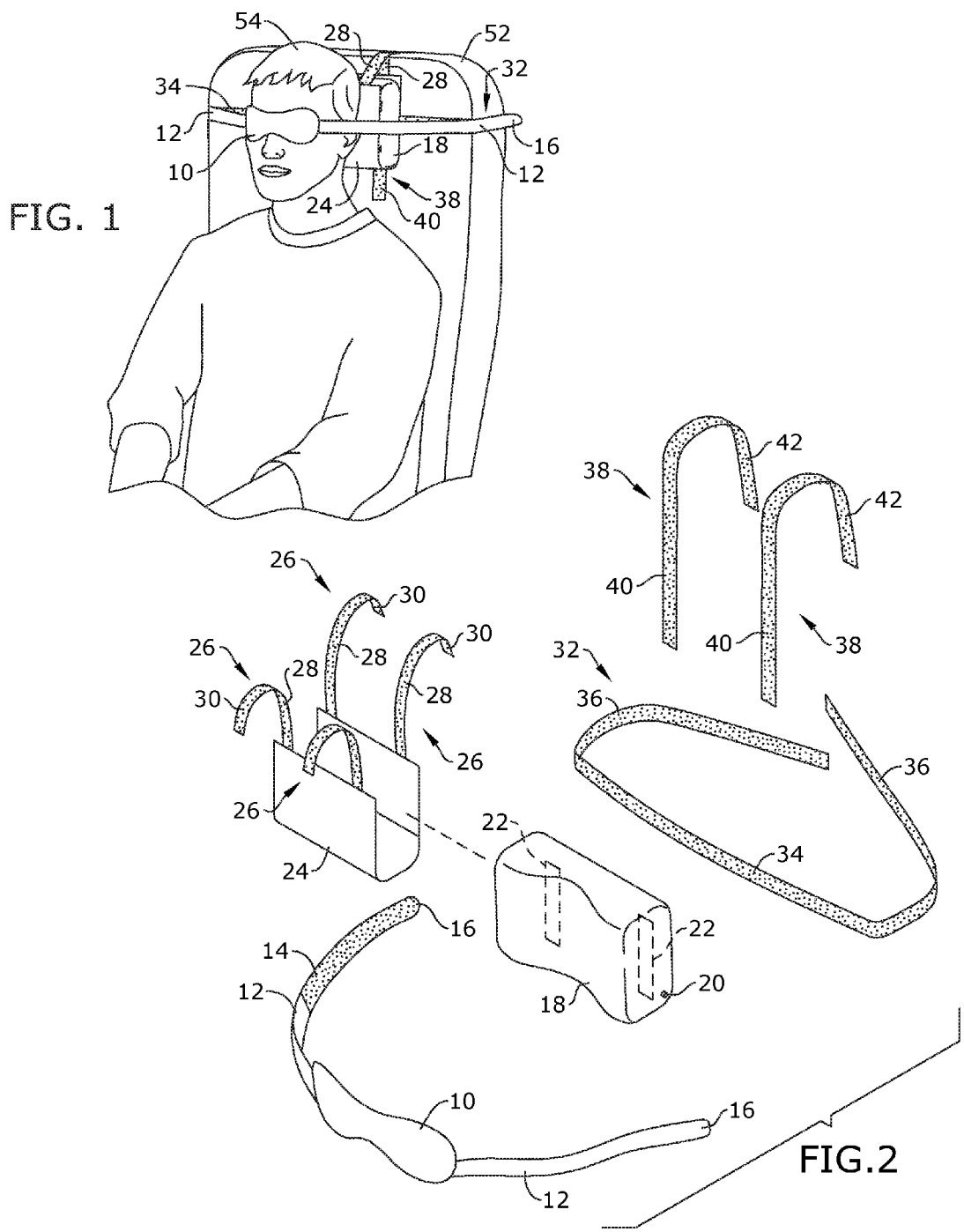

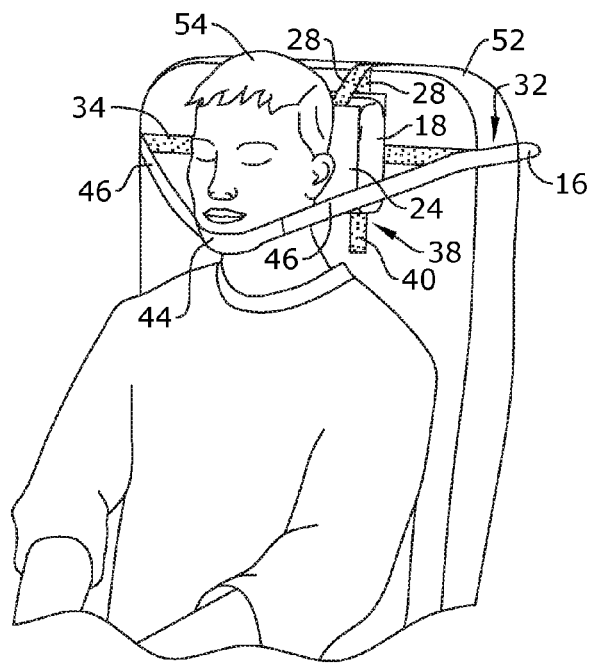
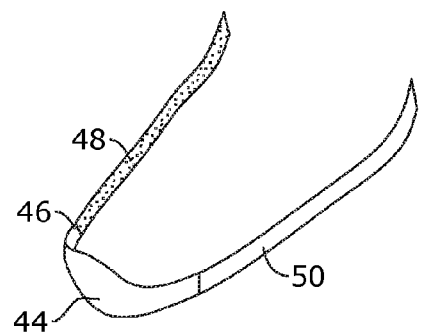
FIG.6
FIG.5
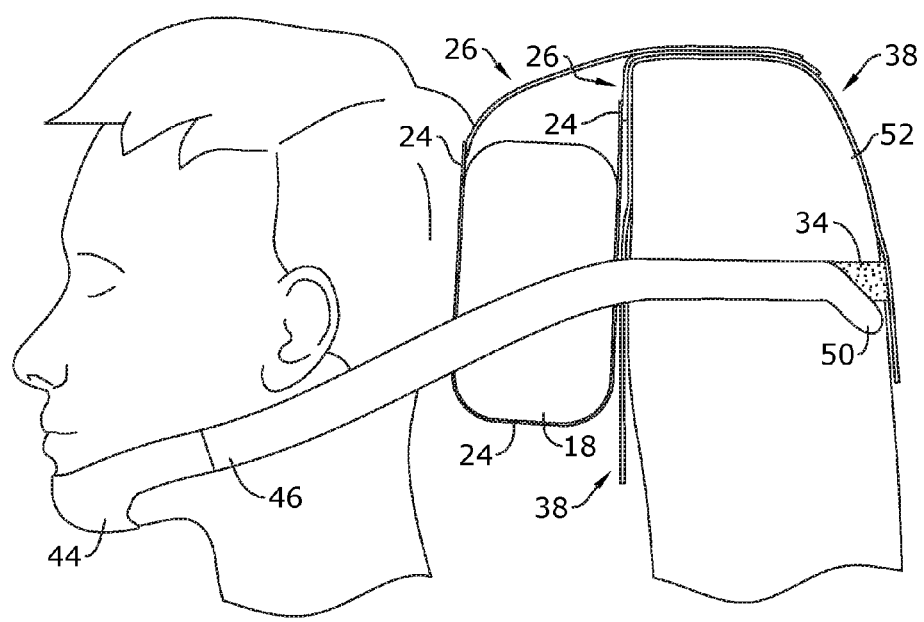
FIG.7

SEAT RESTING APPARATUS

CROSS-REFERENCE TO RELATED APPLICATION

This application claims the benefit of priority of U.S. provisional application No. 62/207,095, filed Aug. 19, 2015, the contents of which are herein incorporated by reference.

BACKGROUND OF THE INVENTION

The present invention relates to sleeping while traveling and, more particularly, to a seat resting apparatus.

When people travel as a passenger on a plane, train, or car, etc., for hours at a time, it is difficult to find a comfortable position in the seat provided. The common neck pillows presently on the market do not meet the need for rest and comfort. They tend to be cumbersome, weighty, and inconvenient and need constant adjusting. Heads tend to fall forward or sideways when trying to sleep or rest. Because of the uncomfortable position, people may develop serious neck issues which can cause pain for several days and at times permanent neck or spinal damage can occur. While attempting to rest or sleep, people can easily fall into the person seated next to them, creating awkward situations. Also, the possibility of snoring is very real, as well as the occasional drool which can be embarrassing.

As can be seen, there is a need for an improved seat resting apparatus for traveling.

SUMMARY OF THE INVENTION

In one aspect of the present invention, a seat resting apparatus comprises: a pillow; a connector operable to connect the pillow to a headrest of a seat; and a face strap comprising a first end and a second end, wherein the face strap is sized to wrap around a user's face and the first end and the second end are connectable to the headrest of the seat.

In another aspect of the present invention, a method of comfortably resting on a seat comprises: attaching a pillow to a headrest of a seat by a connector; providing a face strap comprising a first end and a second end; wresting a head of a user on the pillow; wrapping the face strap around a face of the user; and securing the first end and the second end of the face strap to the headrest.

These and other features, aspects and advantages of the present invention will become better understood with reference to the following drawings, description and claims.

BRIEF DESCRIPTION OF THE DRAWINGS

FIG. 1 is a perspective view of an embodiment of the present invention shown in use;

FIG. 2 is an exploded view of an embodiment of the present invention;

FIG. 5 is a perspective view of an embodiment of the present invention;

FIG. 6 is a perspective view of an embodiment of the present invention; and

FIG. 7 is a side view of an embodiment of the present invention shown in use.

DETAILED DESCRIPTION OF THE INVENTION

Figure 3:
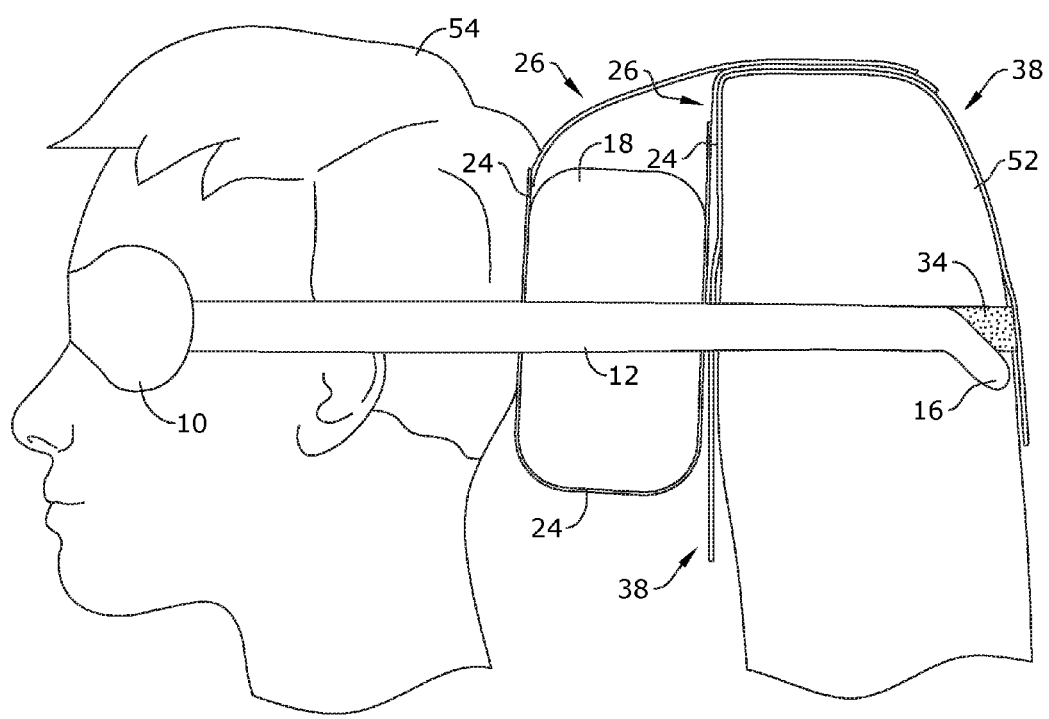
FIG. 3 is a side view of an embodiment of the present invention shown in use.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention provides adjustable support for a user's face as well as a stationary, inflatable pillow that gently keeps a user's head and neck in an upright, comfortable position. The present invention helps users rest or sleep easily while traveling. Finally, the present invention prevents a mouth from hanging open, snoring or drooling, slipping into a neighbor's space, or the possibility of a head tipping into the side window. The risk of neck injuries is eliminated. Those with existing neck problems can rest comfortably. The present invention works with any high back seat. The entire device, including the neck pillow, only weighs a few ounces and stores easily in any purse or travel bag.

For the easiest attachment, the user may be standing or kneeling upon the seat bottom facing the back of your seat. The pillow is first inflated. After the length of horizontal and vertical straps are positioned on the seat back or head rest and attached to pillow straps, the user may then attach the inflatable pillow which has been inserted into the casing. The inflatable pillow can be raised or lowered according the position of the user's neck in that particular seat. At this point the user should seat themselves and take the face strap and attach the face strap to the horizontal strap. If it is too tight, the user can either release the face strap by pulling the tab on the face strap and adjusting the face strap for comfort. If more or less face strap is needed, the user can adjust where the face strap meets horizontal strap. The use of the present invention allows the user to relax and not worry about their neck turning sideways and developing a sore neck or allowing further damage to existing arthritis or other muscle/spine related problems. The user also doesn't have to worry about sliding into a neighbor or being a nuisance with snoring because the chin cap keeps the users mouth closed until chin cap is released. The face strap is easily removed either by pulling the tab or just moving your head forward with slight tension to release the face strap from the horizontal strap.

Referring to FIGS. 1 through 3 and 5 through 7, the present invention includes a seat resting apparatus. The seat resting apparatus includes a pillow 18 connectable to a headrest of a seat 52 by a connector 32, 38. The present invention further includes a face strap 12 having a first end and a second end. The face strap 12 is sized to wrap around a user's face. The first end and the second end attach to the headrest of the seat 52, thereby securing the user's head against the pillow 18.

The connector 32, 38 of the present invention may include a horizontal strap 32. The horizontal strap 32 may include a hooked fastener 34 disposed on an outer surface and a looped fastener 36 disposed on the inner surface. The horizontal strap 32 wraps around the headrest of the seat 52 and the ends of the horizontal strap 32 attach via the hooked fastener 34 and the looped fastener 36. The horizontal strap 32 is horizontally disposed about the headrest of the seat 52.

The connector 32, 38 of the present invention may further include a vertical strap 38, such as a pair of vertical straps 38. Each of the vertical straps 38 may include a hooked fastener 40 disposed on an outer surface and a looped fastener 42 disposed on the inner surface. The vertical straps 38 may wrap around a top of the headrest in a vertical position so that a first end of the vertical straps 38 may be connected to horizontal strap 32 on a first side of the headrest and a second end of the vertical straps 38 may be connected to the horizontal strap 32 on the second side of the headrest via the hooked and looped fasteners 40, 42.

The present invention may further include a pillow case 24. The pillow case 24 may include a sheet forming a U-shaped body when wrapped around the pillow 18. The U-shaped body may include a first upper edge and a second upper edge. A pair of first pillow case straps 26 extend from the first upper edge and a pair of second pillow case straps 26 extend from the second upper edge. Each of the pair of first pillow case straps 26 and second pillow case straps 26 may include a hooked fastener 28 disposed on an outer surface and a looped fastener 30 disposed on the inner surface. Each of the pair of first pillow case straps 26 and second pillow case straps 26 connect with the pair of vertical straps 38 via the hooked fastener 28 and the looped fastener 30.

The pillow 18 of the present invention may include fastener strips 22 that connect with an inner surface of the sheet. Further, the pillow 18 of the present invention may be inflatable. In such embodiments, the pillow 18 is formed of a membrane forming an internal space. A valve 20 may be connected to the membrane leading into the internal space. In such embodiments, the pillow 18 may be pumped and deflated to the user's 54 liking. Further, in a stowed position, the pillow 18 may be completely deflated. The pillow 18 of the present invention may further include an indent to receive the back of the user's head.

As mentioned above, the face strap 12 of the present invention may include a first end and a second end. A looped fastener 14 may be disposed on an inner surface of the face strap 12. The looped fastener 14 may connect with the hooked fastener 34 of the horizontal strap 32. The first end and the second end may be in the form of pull tabs 16 so the user 54 may easily attach and remove the face strap 12 from the headrest. The face strap 12 of the present invention may include a sleeping mask 10 having eye covers. In such embodiments, the eye covers may cover the face of the user 54. In certain embodiments, the face strap 12 may be a chin strap 46. The chin strap 46 may include a chin cup 44 formed to fit over a chin of a user 54. The chin strap 46 may also include the looped fastener 48 and the pull tabs 50 so the user 54 may easily attach and remove the face strap 12 from the headrest.

Broadly, a method of using the present invention may include the following steps: attaching a pillow to a headrest of a seat by a connector; providing a face strap comprising a first end and a second end; wresting a head of a user on the pillow; wrapping the face strap around a face of the user; and securing the first end and the second end of the face strap to the headrest.

Figure 4:
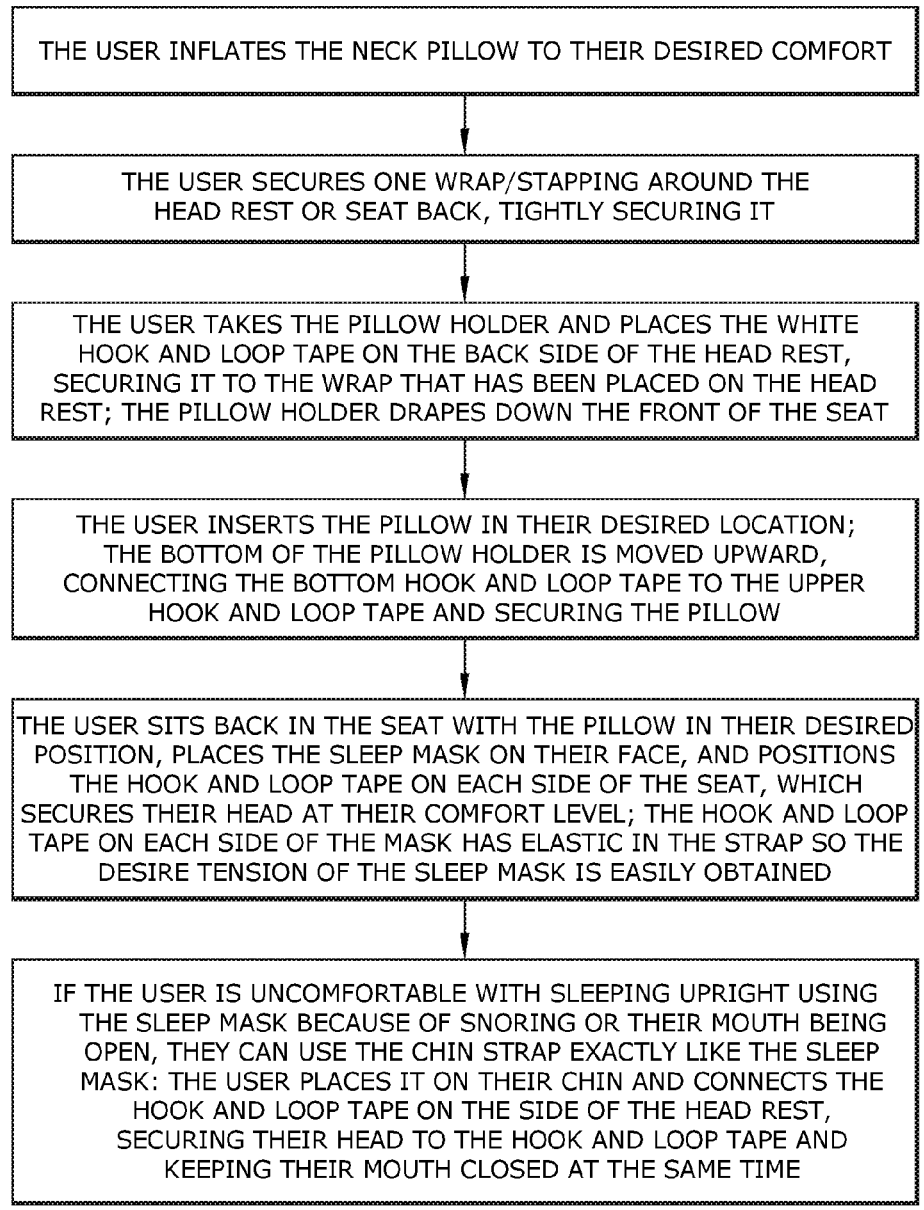
FIG. 4 is a flowchart of a method of using the present invention.

As illustrated in FIG. 4, the method of the present invention may also include the following steps. The user inflates the neck pillow to their desired comfort. The user secures one wrap/strapping around the head rest or seat back, tightly securing it. The user takes the pillow holder and places the hook and loop tape on the back side of the head rest, securing it to the wrap that has been placed on the head rest. The pillow holder drapes down the front of the seat. The user inserts the pillow in their desired location. The bottom of the pillow holder is moved upward, connecting the bottom hook and loop tape to the upper hook and loop tape and securing the pillow. The user sits back in the seat with the pillow in their desired position, places the sleep mask on their face and positions the hook and loop tape on each side of the seat, which secures their head at their comfort level. The hook and loop tape on each side of the mask may have a rubber elasticity so the desired tension of the sleep mask is easily obtained. If the user is uncomfortable with sleeping upright using the sleep mask because of snoring or their mouth being open, they can use the chin strap exactly like the sleep mask. The user places it on their chin and connects the hook and loop tape on the side of the head rest, securing their head to the hook and loop tape and keeping their mouth closed at the same time.

It should be understood, of course, that the foregoing relates to exemplary embodiments of the invention and that modifications may be made without departing from the spirit and scope of the invention as set forth in the following claims.

What is claimed is:

1. A seat resting apparatus comprising:
   a horizontal strap configured to wrap around a front and a rear of a headrest of a seat;
   at least one vertical strap comprising a first end and a second end, wherein the first end is releasably attached to the horizontal strap at the rear of the headrest, wherein the at least one vertical strap is configured to wrap around a top of the headrest so that the second end is connected with the horizontal strap at the front of the headrest;
   a pillow releasably attached to the vertical strap; and
   a face strap comprising a first end and a second end, wherein
   the face strap is sized to wrap around a user's face and the first end and the second end are releasably attached to the horizontal strap.

2. The seat resting apparatus of claim 1, wherein the horizontal strap comprises a hook and loop fastener.

3. The seat resting apparatus of claim 2, wherein the at least one vertical strap comprises a hook and loop fastener.

4. The seat resting apparatus of claim 3, further comprising a pillow case comprising a sheet forming a U-shaped body when wrapped around the pillow, wherein the U-shaped body comprises a first upper edge and a second upper edge, wherein a first pillow case strap extends from the first upper edge and a second pillow case strap extends from the second upper edge, wherein the first and second pillow case straps connect with the at least one vertical strap.

5. The seat resting apparatus of claim 1, wherein the pillow is inflatable and comprises an internal space and a valve leading into the internal space.

6. The seat resting apparatus of claim 1, wherein the face strap comprises a chin cup.

7. The seat resting apparatus of claim 1, wherein the face strap comprises a sleeping mask comprising eye covers.

8. A method of comfortably resting on a seat comprising:
   wrapping a horizontal strap around a front and a rear of a headrest of a seat, thereby connecting the horizontal strap to the headrest;
   attaching a first end of at least one vertical strap to the horizontal strap at the rear of the headrest;
   wrapping the at least one vertical strap over a top of the headrest so that a second end of the at least one vertical strap connects with the horizontal strap at the front of the headrest;
   attaching a pillow to the at least one vertical strap;
   wrapping a face strap around a head of a user, wherein the head of the user is disposed in between the face strap and the pillow; and connecting a first end of the face strap to a first side of the horizontal strap and connecting a second end of the face strap to a second side of the horizontal strap.

9. The method of claim 8, wherein the face strap comprises a sleeping mask comprising eye covers.

10. The method of claim 9, wherein the step of wrapping the face strap around a face of a user comprises wrapping the face strap around eyes of the user.

11. The method of claim 8, wherein the face strap comprises a chin cup.

12. The method of claim 11, wherein the step of wrapping the face strap around a face of a user comprises wrapping the face strap around a chin of the user.

13. A seat resting apparatus comprising:
- a horizontal strap configured to wrap around a front and a rear of a headrest of a seat;
- a pillow;
- a pillow case comprising a sheet wrapped around the pillow forming a U-shape, wherein the U-shape comprises a first upper edge and a second upper edge, wherein a first pillow case strap extends from the first upper edge and a second pillow case strap extends from the second upper edge, wherein the first and second pillow case straps are configured to attach to the headrest of the seat;
- a face strap comprising a first end and a second end, wherein
- the face strap is sized to wrap around a user's face and the first end and the second end are releasably attached to the horizontal strap.

\* \* \* \* \*